(12) United States Patent
Solaun et al.

(10) Patent No.: US 11,751,881 B2
(45) Date of Patent: Sep. 12, 2023

(54) SECUREMENT WIRE WITHSTANDING FORCES DURING DEPLOYMENT OF IMPLANTABLE INTRAVASCULAR TREATMENT DEVICE USING A DELIVERY AND DETACHMENT SYSTEM

(71) Applicant: DePuy Synthes Products, Inc., Raynham, MA (US)

(72) Inventors: Daniel Solaun, Miami, FL (US); Robert Slazas, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 160 days.

(21) Appl. No.: 17/535,971

(22) Filed: Nov. 26, 2021

(65) Prior Publication Data

US 2023/0165588 A1    Jun. 1, 2023

(51) Int. Cl.
 *A61B 17/00* (2006.01)
 *A61B 17/12* (2006.01)

(52) U.S. Cl.
 CPC .. *A61B 17/12145* (2013.01); *A61B 17/12113* (2013.01); *A61B 2017/00526* (2013.01); *A61B 2017/12054* (2013.01)

(58) Field of Classification Search
 USPC ......................................................... 606/191
 See application file for complete search history.

(56) References Cited

U.S. PATENT DOCUMENTS

| | | | |
|---|---|---|---|
| 8,795,316 B2 | 8/2014 | Balgobin et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |

(Continued)

OTHER PUBLICATIONS

European Search Report in counterpart EP Application No. 22 20 9578.8 (8 pp.)(dated Apr. 5, 2023).

*Primary Examiner* — Tan-Uyen T Ho
*Assistant Examiner* — Theodore Le Vu
(74) *Attorney, Agent, or Firm* — COHEN & HILDEBRAND, PLLC (57) ABSTRACT

Delivery and detachment system for an implantable intravascular treatment device, the system including an outer delivery tube and a proximal inner tube telescopically slidable within the lumen of the outer delivery tube. The proximal inner tube has a weld window radially inward cutout defined therein along an axial section between the proximal and distal ends. A securement wire disposed axially within the lumen of the proximal inner tube is secured to an inner wall of the lumen of the proximal inner tube via at least one supplemental connection point coinciding with the weld window. Also, the method for making the delivery and detachment system wherein one or more positioning wires threaded through the lumen of the proximal inner tube are manipulated to force the securement wire and the proximal inner tube in direct physical contact with one another along an axial section coinciding with the weld window.

21 Claims, 7 Drawing Sheets

(56) References Cited

U.S. PATENT DOCUMENTS

| | | |
|---|---|---|
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0250150 A1 | 9/2018 | Majercak et al. |
| 2018/0280667 A1* | 10/2018 | Keren ................... A61B 17/11 |
| 2020/0046370 A1 | 2/2020 | Gorochow |
| 2020/0397444 A1* | 12/2020 | Montidoro ........ A61M 25/0662 |
| 2021/0015484 A1 | 1/2021 | Lorenzo |
| 2021/0346002 A1 | 11/2021 | Lorenzo et al. |
| 2022/0054136 A1* | 2/2022 | Blumenstyk ..... A61B 17/12022 |

* cited by examiner

SECUREMENT WIRE WITHSTANDING FORCES DURING DEPLOYMENT OF IMPLANTABLE INTRAVASCULAR TREATMENT DEVICE USING A DELIVERY AND DETACHMENT SYSTEM

FIELD OF THE INVENTION

The present invention relates to a delivery and detachment system for an implantable intravascular treatment device (e.g., embolic coil) used during an endovascular treatment or procedure. In particular, the present invention is directed to a delivery and detachment system for implantation of an implantable intravascular treatment deice (e.g., embolic coil) in the intravascular treatment of a brain aneurysm. In the present inventive improved delivery and detachment system the securement wire is able to withstand forces during detachment/deployment of the implantable intravascular treatment device (e.g., embolic coil) at a target site.

DESCRIPTION OF RELATED ART

Figure 1:
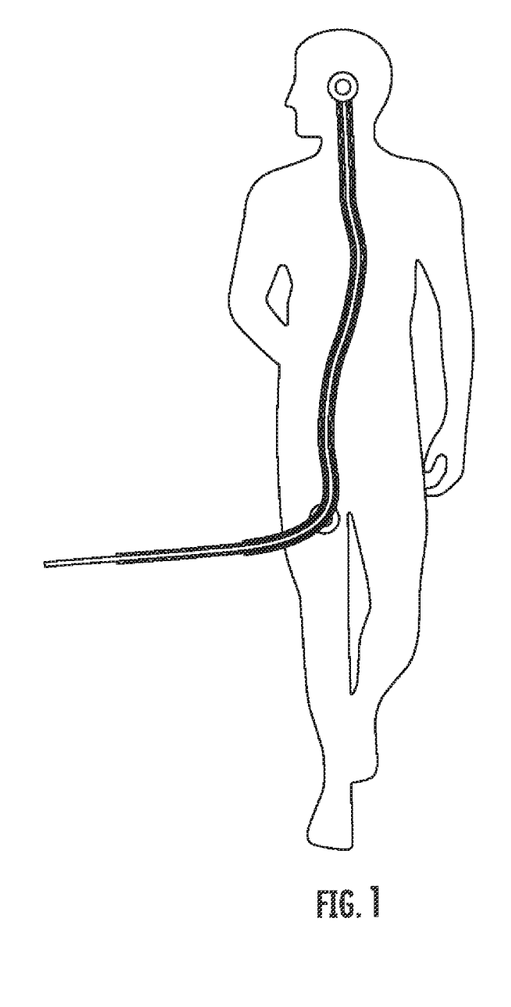
FIG. 1 depicts a pathway or route of navigation by the guide catheter through the femoral artery to a target site in the brain.
Figure 2:
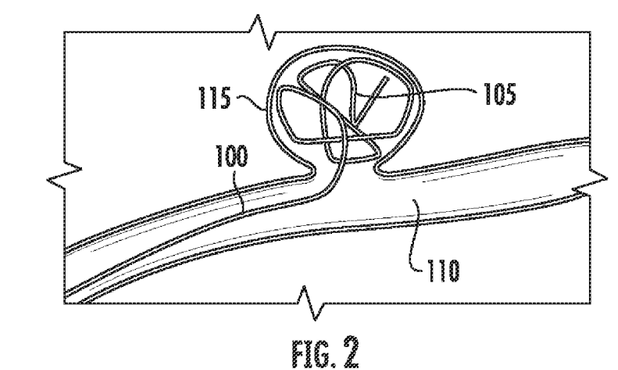
FIG. 2 illustrates a single implantable intravascular treatment device (e.g., embolic coil) deployed/deposited in an aneurysm using the detachment and detachment system withdrawn.
Figure 3:
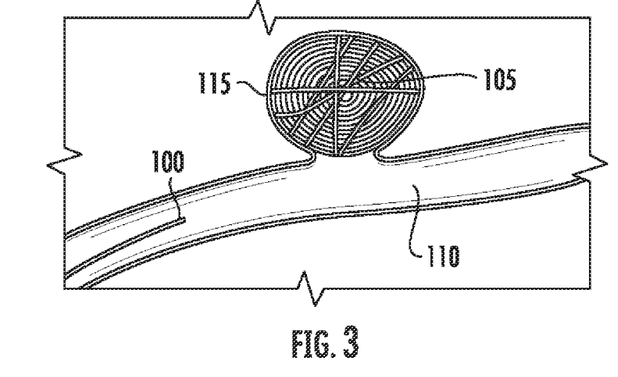
FIG. 3 represents an aneurysm packed with a plurality of embolic coils after withdraw of the microcatheter.
Figure 4:
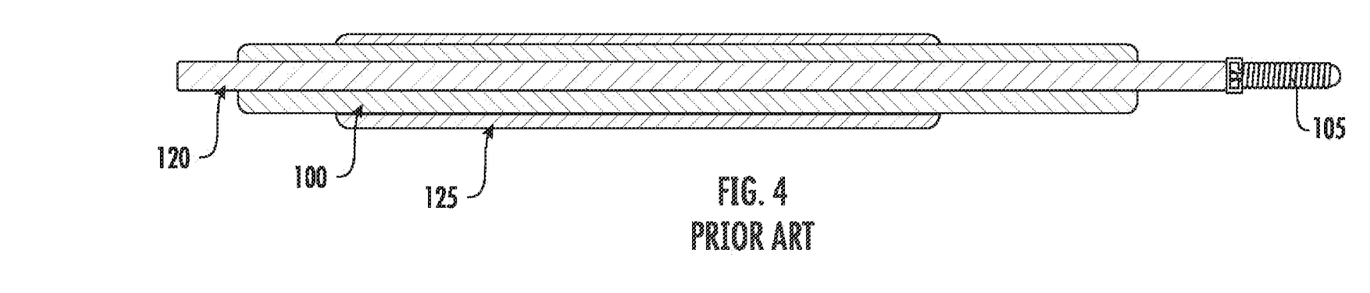
FIG. 4 is a side view of a Prior Art delivery and detachment system loaded with an embolic coil during an exemplary application in which the delivery and detachment system is disposed within a microcatheter which, in turn, is disposed in a guide catheter.

Implantable intravascular treatment devices are commonly used in endovascular procedures or treatments of various vascular ailments, for example, brain aneurysms. Typically, a guide catheter is inserted into the femoral artery in patient's leg and, while guided by imaging, navigated through the vessel to the target site in the brain (e.g., a proximal side of the aneurysm), as shown in FIG. 1. In a particular application or use, with the distal end of the guide catheter 125 properly positioned on a proximal side of the aneurysm, a microcatheter 100 may be tracked through the guide catheter to the proximal side of the aneurysm (FIG. 4). Next, a delivery and detachment system 120 loaded with an implantable intravascular device (e.g., embolic coil) 105 is introduced via the microcatheter 100 and advanced to the proximal side of the aneurysm. During delivery to the target site, the implantable intravascular treatment device (e.g., embolic coil) 105 is secured within the delivery and detachment system 120 via a securement wire (e.g., pull wire). Once properly positioned at the target site (e.g., at the location on a proximal side of the aneurysm) the securement wire is translated (e.g., axially pulled in a proximal direction) releasing the implantable intravascular treatment device (e.g., embolic coil) to be deposited within the aneurysm (FIG. 2 showing a single deposited embolic coil). This process is repeated until the area of the vessel with the weakened wall is tightly packed with numerous embolic coils occluding blow flow thereto thereby preventing rupture, as depicted in FIG. 3.

The present invention is directed to an improved mechanical delivery and detachment system in which the implantable intravascular treatment device (e.g., embolic coil) is releasably secured to the distal end thereof via a securement wire that itself is robustly attached along an axial section thereof to the inner wall of the proximal inner tube via one or more supplemental connection points able to withstand forces during deployment.

SUMMARY OF THE INVENTION

An aspect of the present invention is directed to an improved mechanical delivery and detachment system in which the implantable intravascular treatment device (e.g., embolic coil) is releasably secured to the distal end thereof via a securement wire that itself is robustly attached along an axial section thereof to the inner wall of the proximal inner tube via one or more supplemental connection points able to withstand forces during deployment.

Another aspect of the present invention relates to a delivery and detachment system for an implantable intravascular treatment device, wherein the system includes: an outer delivery tube having a proximal end, an opposite distal end, and a lumen defined axially therein; and a proximal inner tube having a proximal end, an opposite distal end, and a lumen defined axially therein. The proximal inner tube is telescopically slidable within the lumen of the outer delivery tube and has a weld window radially inward cutout defined therein along an axial section thereof between but not including the proximal and distal ends. The system further including a securement wire disposed axially within the lumen of the proximal inner tube, wherein the securement wire is secured to an inner wall of the lumen of the proximal inner tube via at one supplemental connection point coinciding with the weld window.

A still further aspect of the present invention is directed to a method of making the delivery and detachment system for an implantable intravascular treatment system described in the preceding paragraph. Initially, the proximal inner tube is assembled telescopically in the lumen of the outer delivery tube so that the proximal end of the proximal inner tube extends beyond the proximal end of the outer delivery tube without concealing the weld window. Then, the securement wire and at least one positioning wire is threaded in a direction from the distal end to the proximal end of the proximal inner tube through the lumen of the proximal inner tube until the proximal end of each of the securement wire and the at least one positioning wire extends beyond the proximal end of the proximal inner tube. Next, the securement wire is forced in direct physical contact with an inner wall of the lumen of the proximal inner tube coinciding with the weld window by manipulating the securement wire and/or the at least one positioning wire. Within the weld window, at least one supplemental connection point is created between the securement wire and the inner wall of the lumen of the proximal inner tube along an axial section in direct physical contact with one another. Then the at least one positioning wire is withdrawn in a proximal direction from the proximal inner tube.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which.

DETAILED DESCRIPTION OF THE INVENTION

In the description, the terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot" or "blockage" are used interchangeably.

Figure 5:
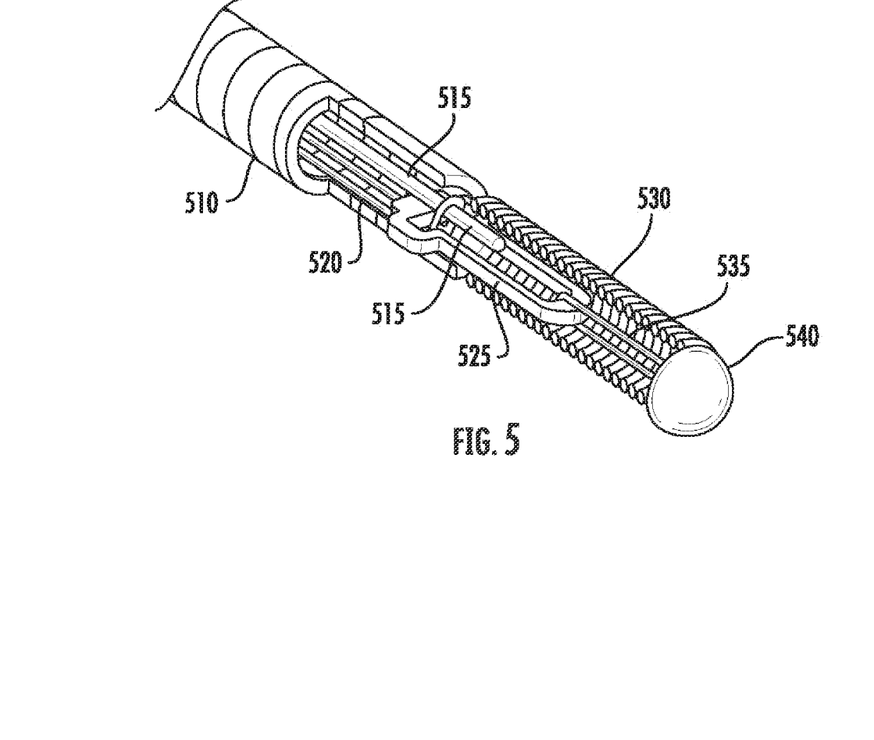
FIG. 5 is a perspective cut away view of a distal section of an exemplary mechanism including a securement wire for releasably securing the implantable intravascular treatment device (e.g., embolic coil) to the distal end of the present inventive delivery and detachment system.
Figure 10A:
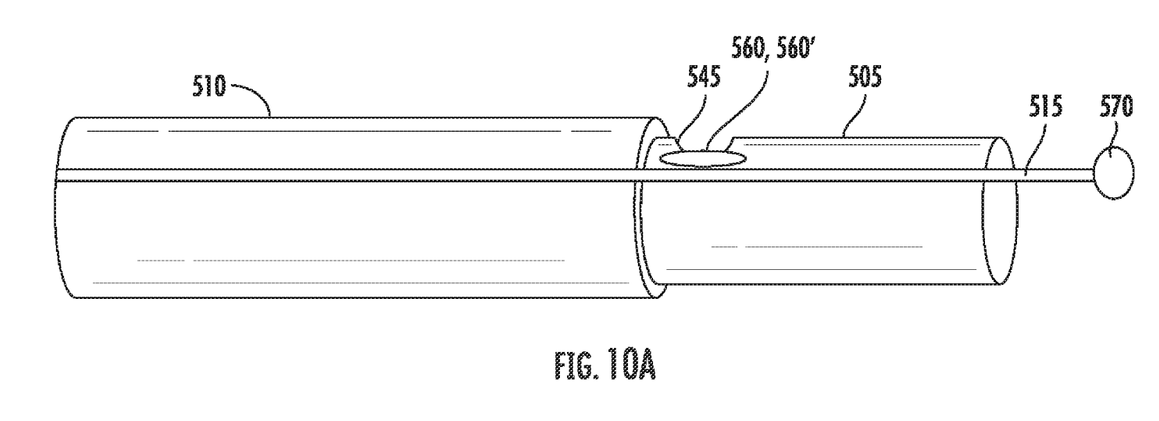
FIG. 10A is a side view representation of the securement wire welded to the proximal inner tube together as a unit assembled in the outer delivery tube, prior to loading the implantable intravascular device.

During an endovascular treatment procedure (e.g., coil embolization), it is desirable for the delivery and detachment system to reliably and accurately deliver the implantable intravascular treatment device (e.g., embolic coil) to a precise location or target site (e.g., aneurysm) within a vessel or artery; and, once properly positioned, ensure complete deployment (detachment or separation) of the implantable intravascular treatment device from the system. Referring to FIG. 10A, the delivery and detachment system comprises a proximal inner tube (e.g., proximal member) 505 telescopically slidable within an axial lumen of an outer delivery tube (e.g., pusher) 510. A securement wire (e.g., pull wire) 515 extending axially through the lumen of the delivery and detachment system is fixedly attached at its proximal end to the proximal end of the proximal inner tube 505 via a proximal bead 570. An opposite distal end of the securement wire 515 is releasably secured to the implantable intravascular device (e.g., embolic coil) 530. Attachment of the implantable intravascular treatment device (e.g., embolic coil) to the securement wire is via a purely mechanical securement mechanism (e.g., translated release), that is, a mechanism releasable exclusively by translation (i.e., pulling in a linear (axial or longitudinal) direction on the securement wire 515 in a proximal direction (without the need for application of electrical and/or thermal heat)). In the exemplary configuration of the distal end of the delivery and detachment system depicted in FIG. 5 the mechanical securement mechanism includes a U-shape loop wire 520 extending in a proximal direction through the lumen 508 of the delivery and detachment system. The U-shape loop wire 520 wire has two proximal ends extending in a proximal direction and affixed to the delivery and detachment system while its opposite closed distal end (forming a loop) is bent upwards threaded through an opening of a proximal key 525. A sufficient amount of the closed distal end of the U-shape loop wire 520 projects upwards through the opening of the proximal key 525 forming a loop (eyelet) through which the free distal end of the securement wire 515 is axially slidable/passable/threadable therethrough. In turn, the distal end of the proximal key 525 is receivable within an open proximal end of an embolic coil 530 secured in position thereto by a stretch restraint fiber 535 at a proximal end threaded through the opening at the distal end of the proximal key 525 and attached at an opposite distal end to a distal bead or cap 540. Thus, when the distal end of the securement wire 515 is engaged within the closed distal end of the U-shape loop wire 520 the implantable intravascular treatment device (e.g., embolic coil) 530 is secured to the distal end of the delivery and detachment system.

Minimal, if any, restraint prohibiting or minimizing dislodgement of the securement wire 515 from the proximal inner tube 505 is provided by the proximal bead 570 primarily serving to aid easy insertion in the delivery and detachment device. During detachment of the implantable intravascular treatment device when forces imposed on the securement wire may exceed that of the break load of the wire itself, a high probability exists of unintended detachment of the securement wire 515 from the proximal inner tube 505 when the proximal bead 570 is the sole point connecting the two components. The design of the present inventive delivery and detachment system provides one or more supplemental connection points (e.g., spot welds) between the securement wire and the proximal inner tube thereby exceeding in overall strength the connection provided by the proximal bead 570 alone.

A laser cutout made radially inward in the proximal inner tube 505 creates a weld window 545 providing an access point through which the two components (securement wire 515 and proximal inner tube 505) are secured together via the creation of one or more supplemental connection points (e.g., one or more supplemental spot welds). These one or more supplemental connection points being in addition to that of the proximal bead 570 disposed at the proximal end of the securement wire 515 securing it to the proximal end of the proximal inner tube 505. In contrast to the arrangement of the proximal bead 570 located at the proximal end of the securement wire 515, the one or more supplemental connection points are located along an axial section (between, but not including the proximal and distal ends) of the securement wire 515. The length in the axial/longitudinal direction as well as the length in a lateral direction that defines the weld window cutout in the proximal inner tube 505 is selected, as desired, with several competing factors. On the one hand, the cutout is sufficient in size to: (i) visibly position therein the securement wire in direct physical contact with the inner wall of the proximal inner tube; and (ii) allow for creation of the desired size and number of one or more supplemental connection point(s) (e.g., laser spot weld(s)) between the two components (e.g., the securement wire and the inner wall of the proximal inner tube)) to achieve a desired target strength. While on the other hand, the proximal inner tube retains sufficient rigidity or strength (i.e., higher tensile strength—less frangible). Addressing each factor, clearly a laser cutout sufficiently large in size (width in a lateral direction and/or length in an axial direction) is selected to accommodate the desired quantity and size spot weld(s) to prohibit or minimize detachment of the securement wire from the proximal inner tube, while a cutout too large in size may negatively diminish or weaken the integrity/rigidity (i.e., lower tensile strength—more frangible) of the proximal inner tube. Keeping these competing factors in mind, by way of example, the cutout may be designed with a width in a lateral direction in a range of approximately 0.0019 inches-approximately 0.0045 inches and a length in an axial direction in a range of approximately 0.012 inches-approximately 0.016 inches. In addition, the proximal edge of the most proximal weld window is preferably ≥approximately 1 mm in an axial direction from the proximal end/tip of the proximal inner tube.

Prior to creating the one or more lap spot welds (the one or more supplemental connection points) the securement wire 515 and proximal inner tube 505 are forced in direct physical contact with one another along an axial section (between but not including the respective proximal and distal ends). This is accomplished by filling the space in the lumen of the proximal inner tube 505 having the securement wire 515 threaded therethrough with one or more positioning wires 550, 550' as necessary to ensure proper fitment. The one or more positioning wires 550, 550' are manipulated forcing the securement wire 515 in direct physical contact against the inner wall of the proximal inner tube 505 along an axial region coinciding (aligned) with the weld window 545 so that one or more secure spot welds (supplemental connection point(s)) 560, 560' therebetween may be created.

Figure 6A:
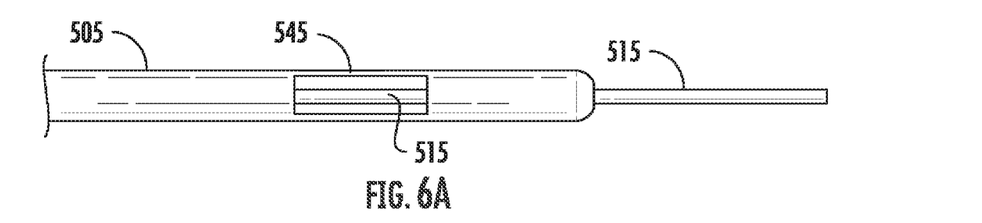
FIG. 6A depicts the proximal inner tube passing over the securement wire.
Figure 6B:
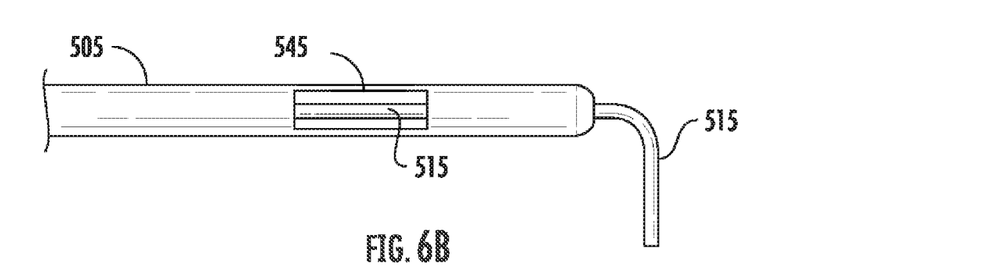
FIG. 6B illustrates the bending of the portion of the proximal end of the securement wire emerging/exiting from the proximal end of the proximal inner tube.

First, during assembly as the proximal inner tube 505 with the weld window 545 cutout defined radially inward therein is pulled over the securement wire 515 (FIG. 6A) (i.e., the securement wire 515 is threaded starting from the distal end to the proximal end of the proximal inner tube 505) whereupon the portion of the proximal end of the securement wire 515 emerging/exiting from the proximal end of the proximal inner tube 505 is bent at an angle (e.g., ≤90°) (FIG. 6B illustrating the proximal end of the proximal inner tube). Next, one or more positioning wire(s) 550, 550' are threaded either one at a time or simultaneously all together at the same time through the lumen of the proximal inner tube 505 with the securement wire 515 already threaded therethrough. It may be difficult to thread more than one positioning wire through the lumen of the proximal inner tube simultaneously at the same time. Moreover, it is contemplated that in order to obtain the optimum tightest fit multiple positioning wires differing in diameter may be employed through a series of trials or experimentation. For example, following insertion of the securement wire 515, next threaded through the lumen of the proximal inner tube 505 is a first positioning wire 550 having a diameter of approximately 0.0022". In a first attempt, a second positioning wire 550' of the same diameter (approximately 0.0022") may be tried. If that size is too large in diameter to fit during a second attempt another wire having a slightly reduced diameter (e.g., 0.002") may be tried. Once again, if unsuccessful another wire with an even smaller diameter (e.g., 0.018") is attempted. This experimentation through multiple attempts or trials is repeated until the optimum tightest fitment is realized.

Figure 6C:
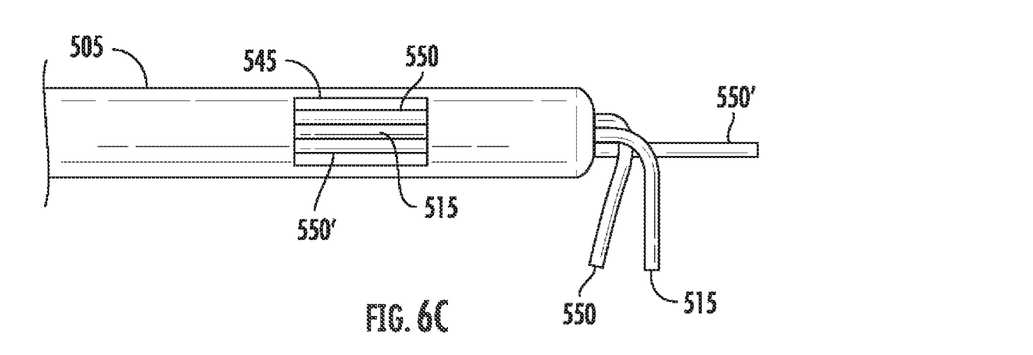
FIG. 6C represents an exemplary proximal inner tube and the securement wire threaded therethrough together as a unit being pulled over a pair of positioning wires.
Figure 6D:
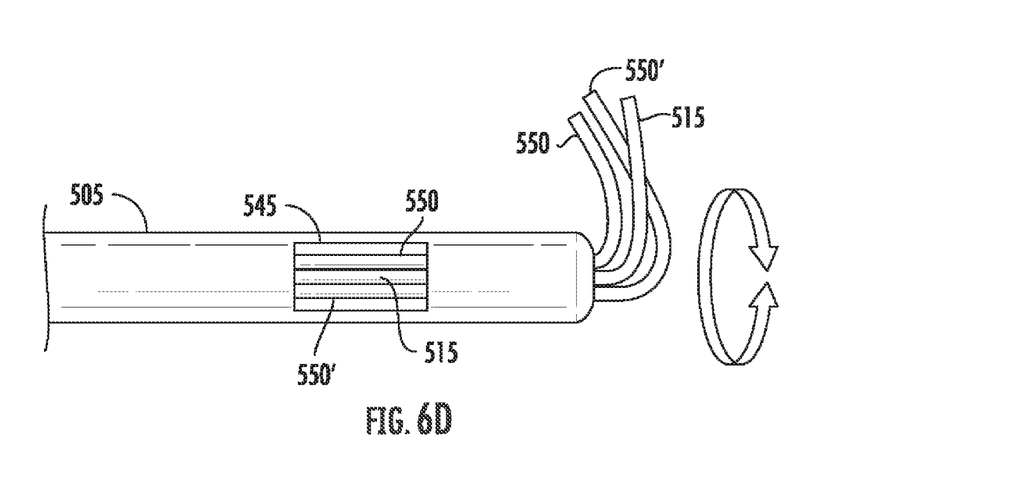
FIG. 6D depicts the manipulation of one or more of the wires (e.g., securement wire and pair of positioning wires) to force the securement wire in direct physical contact with the inner wall of the proximal inner tube along an axial section coinciding with the weld window.
Figure 6E:
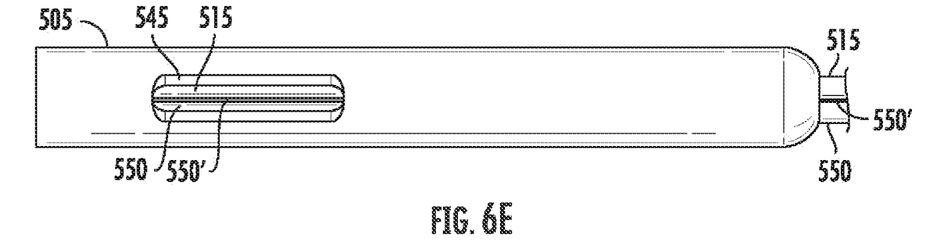
FIG. 6E is a side view of the proximal inner tube showing the securement wire and inner wall of the proximal inner tube in direct physical contact along an axial section coinciding with the weld window (hereinafter referred to as the "securing position")
Figure 6F:
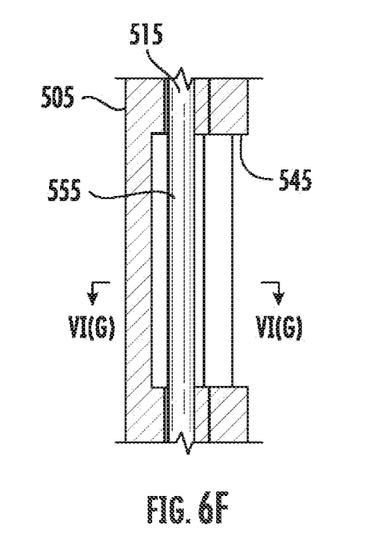
FIG. 6F is a side view of the securement wire in the securing position (i.e., forced in direct physical contact with the inner wall of the proximal inner tube along an axial section coinciding with the weld window) (the positioning wires are not shown)

In the exemplary process in FIG. 6C, two positioning wires 550, 550' are sequentially threaded one at a time through the lumen of the proximal inner tube 505 and the emerging/exiting proximal ends of each positioning wire is bent in similar fashion to that of the securement wire 515 (FIG. 6C). The proximal inner tube 505 is held in place via a chuck. While being observed through the weld window 545, any one or more of the three wires (e.g., the single securement wire 515 and one or both of the positioning wires 550, 550') are manipulated (e.g., rotated, twisted, or maneuvered) (FIG. 6D) with the goal of within the weld window 545 forcing an axial section of the securement wire 515 in direct physical contact with the inner wall of the proximal inner tube 505. Hereinafter such intended placement or positioning of the securement wire when achieved is referred to as the "securing position" (FIG. 6E). When properly located in the securing position the axial section of the securement wire 515 in direct physical contact with the inner wall of the proximal inner tube 505 is aligned/coincides/overlaps with the weld window 545 (FIG. 6E) serving as an access point for performing the one or more spot welds (one or more supplemental connection points). Preferably, the emerging/exiting proximal ends of the respective securement wire 515 and positioning wire(s) 550, 550' extend sufficiently beyond the end of the proximal inner tube (e.g., by at least approximately 1 cm) to allow for easy manipulation of the wires. FIG. 6F is a side view of the proximal inner tube 505 with the securement wire 515 arranged in the securing position (the positioning wires are not shown). Line 555 denotes the axial section of direct physical contact of the securement wire 515 and the inner wall of the proximal inner tube 505. Sequential (one after the other) insertion (threading) of each positioning wire through the lumen of the proximal inner tube (starting from the distal end and exiting from the proximal end) advantageously allows for the optimum tightest fit. Following the securement wire, two positioning wires threaded independently, one after the other, is illustrated and described, but any number of one or more positioning wires may be used to realize the optimum tightest fit. As a result of the tolerances on the inner and outer diameter of the proximal tube the sequential insertion of each positioning wire results in a desirable customized fit per piece. Despite such advantage, nevertheless the securement wire and one or more positioning wire(s) may alternatively simultaneously (all together as a unit at the same time) be threaded through the lumen of the proximal inner tube.

Figure 6G:
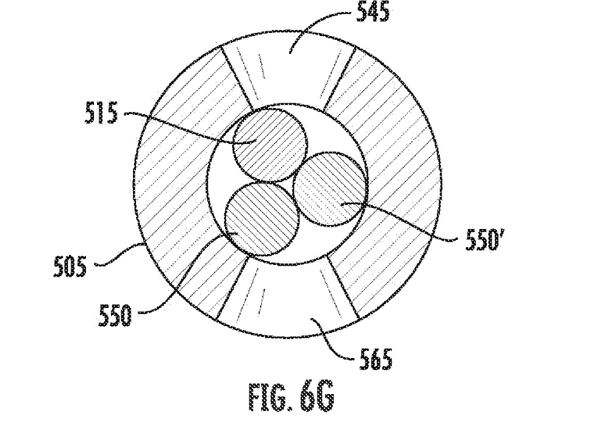
FIG. 6G is a radial cross-sectional view along lines VI(G)-VI(G) of FIG. 6F illustrating the securement wire in the securing position prior to being welded to the inner wall of the proximal inner tube.
Figure 6H:
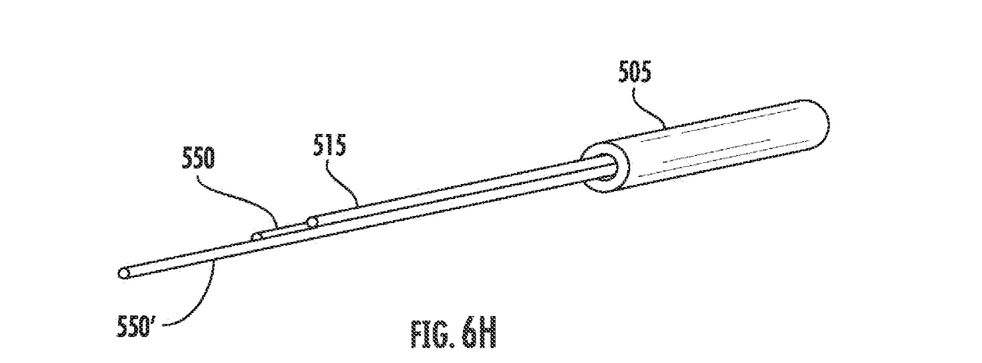
FIG. 6H is an isometric view of the simultaneous threading of three wires (e.g., securement wire and pair of positioning wires) together as a unit through the proximal inner tube.

Once the securement wire 515 is maneuvered to the securing position (i.e., in direct physical contact along an axial section with the inner wall of the proximal inner tube 505), as depicted in FIGS. 6E, 6F & 6G, one or more spot weld(s) 560, 560' (supplemental connection points) consecutive in series (one after the other in an axial direction) is created securing the two components to one another. Any number of one or more spot welds may be made. The greater the quantity of spot welds the more robust or stronger the connection or attachment between the securement wire 515 and proximal inner tube 505. In the case of a single spot weld, if that single bond ruptures or breaks no other welds exist to maintain the two components secured to one another. In the case of more than one spot weld, in the event of rupture or breakage of one or more of those bonds, those remaining spot weld bonds ensure that the securement wire and proximal inner tube nevertheless remain secured together. However, the quantity of individual spot welds arranged axially consecutively in series is limited by the size of the real estate (footprint) available with such a miniature component and the dimensions of the weld window 545 through which access is gained for creation of the multiple spot welds. The larger the size of the weld window both length in an axial direction and width in a lateral direction weakens the strength and rigidity of the proximal tube, as discussed previously in detail.

Figure 7A:
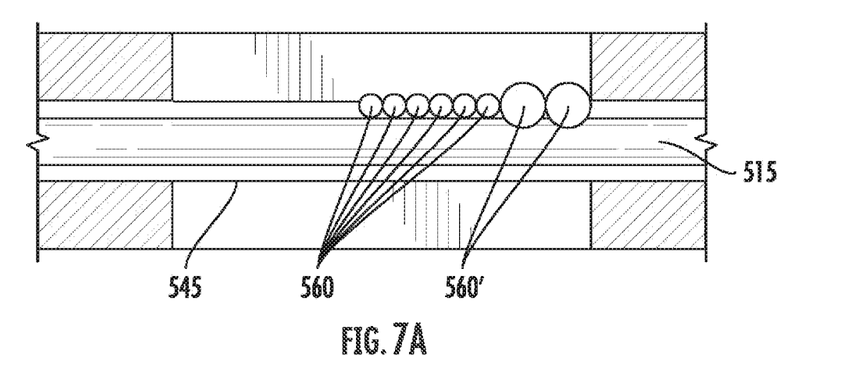
FIG. 7A is a top view of an exemplary proximal inner tube with a laser cut weld window through which is visible a series of 8 spot welds.
Figure 7B:
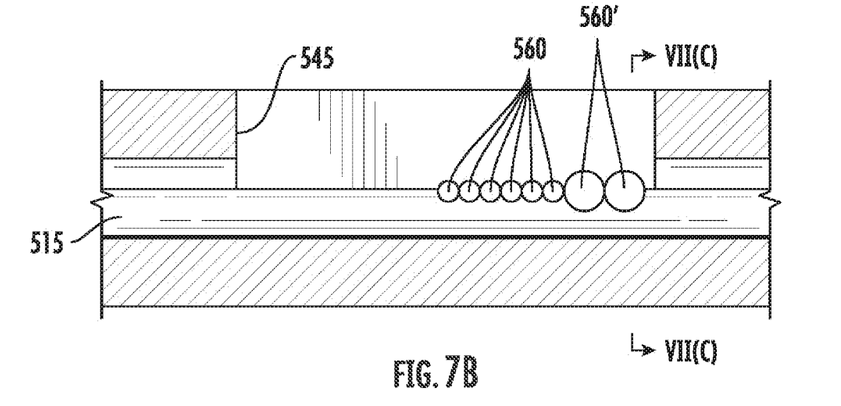
FIG. 7B is the side view of the proximal inner tube of FIG. 7A.
Figure 7C:
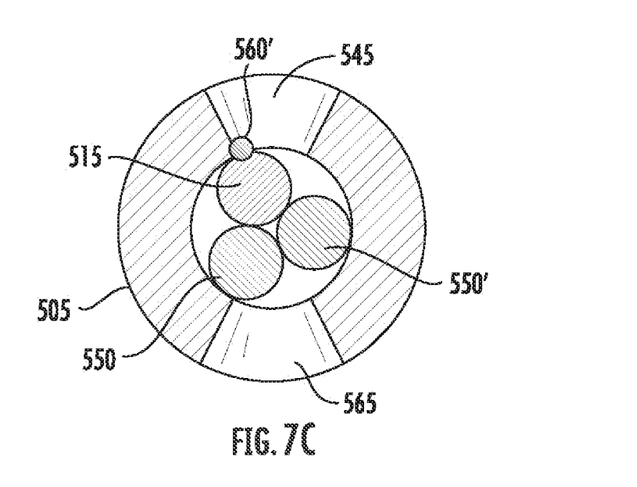
FIG. 7C is a radial cross-sectional view along lines VI((C)— VII(C) of FIG. 7B.

FIGS. 7A & 7B depict respective top and side views of the weld window 545 of the proximal inner tube 505 with an exemplary 8 total spot weld bonds 560, 560' arranged consecutively in series in an axial direction along the axial section in which the securement wire 515 (e.g., having a diameter of approximately 0.0018") is forced by the positioning wires 550, 550' in direct physical contact with the inner wall of the proximal inner tube 505. As previously mentioned, any number of one or more spot welds are possible. More than one spot weld bond is preferred so that in the event of rupture or breakage of one of the distal spot welds those remaining spot welds in a proximal direction relative thereto ensure that the securement wire nevertheless remains secured to the proximal inner tube. The number, size, and arrangement of each of the spot weld bonds may be varied, as desired. All, some, or none of the spot welds may be the same in size and strength. The arrangement of all, some, or none of the spot welds may be uniformly or non-uniformly spaced apart from one another in an axial direction.

To prevent the unintentional welding of the positioning wires when creating the lap spot welds (one or more supplemental connection points), the positioning wires 550, 550' may be made of a heat resistant material or coated with a lubricous outer layer (e.g., Polytetrafluoroethylene (PTFE)). Once the desired weld bonds (one or more supplemental connection points) have been created, the positioning wires may be easily withdrawn in a proximal direction. In the exemplary embodiment in FIGS. 7A & 7B (depicting top and side views respectively with the positioning wires withdrawn), there is a series of 8 total spot weld bonds including two stronger (larger in size) spot welds 560' (the two, equal in size, larger circles to the right are closest to the proximal end of the securement wire 515) relative to that of each in the series of 6 equal in size weaker (smaller in size) spot welds 560 following thereafter in a distal direction. Several advantages are realized via configuring the series of multiple spot welds so as not all uniform in size and strength, as in the example depicted in FIGS. 7A & 7B. Specifically, the 2 largest in size and strongest in strength spot welds 560' (positioned closest to the proximal end—furthest to the right) act as a strain relief for the securement wire 515 preventing or minimizing breakage or rupture thereof. While the quantity of 6 smaller in size and weaker in strength spot welds 560 axially arranged one after the other in series in a distal direction following thereafter ensure connection between the components (e.g., securement wire and proximal inner tube) despite rupture or breakage of one or more of the smaller/weaker spot welds starting from the distal most end (furthest to the left in FIGS. 7A & 7B). Furthermore, when employing more than one smaller/weaker spot weld the load is desirably more uniformly distributed or split among the welds thereby reducing the probability of breakage or rupture of any one weld bond.

Still referring to FIGS. 7A & 7B, starting from the proximal end, the 2 melt "pools" of material represent distinct spot welds 560' each larger in size and stronger in strength (relative to the subsequent 6 spot welds 560 arranged distally thereof) using a laser (e.g., Nd:YAG laser) at a relatively higher power setting. During the welding process an inert gas (e.g., argon gas) is preferably used to prevent oxidation. Such relatively large/strong spot welds, however, come at a cost of damaging/weakening the securement wire. To minimize such damage/weakening of the securement wire, using the same laser set at a lower power setting the subsequent 6 individual spot welds 560 each smaller in size and weaker in strength (relative to the previously mentioned two larger/stronger spot welds 560') provide reinforced strength with de minimis, if any, further damage/weakening of the securement wire. In the example of FIGS. 7A & 7B, starting from the proximal end, the first two welds 560' (two largest spot welds to the right) are created using a Nd:YAG laser having a higher output power (e.g., 30 W-35 W) at a duration between 0.20 ms-0.25 ms generating 0.007J square pulses. Continuing in a distal direction, the next three welds 560 (starting from the proximal end) are created using the Nd:YAG laser at a lower/reduced output power (e.g., 25 W-30 W) for the same duration (0.20 ms-0.25 ms) generating 0.005J square pulses. Still further in a distal direction, the remaining three welds 560 (furthest from the proximal end—furthest to the left) are created using the same parameters as that of the lower/reduced output power (e.g., 25 W-30 W) but now with the laser beam out of focus (e.g., 0.4 mm-0.5 mm, out of focus). The proximal bead 570 securing the proximal end of the securement wire to the proximal end of the proximal inner tube may be made at the same time as the supplemental connection points using the same laser, for example, at an output power of 600-700 W at a duration of 0.4 ms-0.5 ms.

Thus, the desired size and strength of each spot weld (supplemental connection point) may be realized by varying any one or more of the parameter settings (e.g., travel speed, current, and/or voltage). Specifically, the higher power and greater length of time the larger in size and stronger the spot weld (supplemental connection point). In addition to varying such power parameter settings, the laser beam may be focused or defocused, wherein the energy is diluted when the laser is defocused in comparison to that while focused. In FIGS. 7A & 7B, for example, the 2 largest spot welds 560' having the higher power setting are formed with the laser beam focused, while of the smaller 6 spot welds 560 are created at the lower power setting. Among the 6 smaller spot welds 560 the 3 closest to the proximal end/tip of the proximal inner tube (those three smaller spot welds 560 furthest to the right) are formed while the laser beam is focused while the 3 furthest from the proximal end/tip of the proximal inner tube (the remaining three smaller spot welds 560 furthest to the left) are formed with the laser beam defocused. Focusing or defocusing of the laser beam is yet another parameter that may be used, as desired, to achieve the desired strength of any one of the welds.

Figure 9:
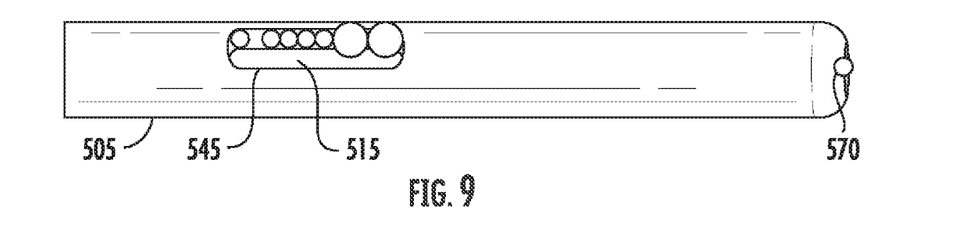
FIG. 9 is a side view of an alternative configuration of 7 spot welds wherein the spot weld furthest from the proximal end of the securement wire (furthest to the left) has a larger separation distance in an axial direction relative to the next adjacent spot weld in comparison to the separation distance in an axial direction between any other adjacent spot welds in a proximal direction.

If more than one weld is created, the strength of each weld may be selected, as desired. For example, the strength of each weld may be selected to decrease with the weld closest to the proximal end/tip of the proximal inner tube being the strongest and the weld furthest from the proximal end/tip of the proximal inner tube being the weakest. Not only strength but spacing or arrangement of the welds may also be selected, as desired. In the exemplary configuration depicted in FIGS. 7A & 7B, the 6 weaker spot welds 560 (i.e., the 6 smaller diameter circles to the left of the 2 larger circles) are arranged consecutively in series in an axial direction with each spot weld arranged substantially equidistant from the adjacent spot weld. However, this need not necessarily be so. As illustrated in the exemplary configuration in FIG. 9 having 7 spot welds, the separation distance in an axial direction of the spot weld furthest from the proximal end/tip of the inner tube (i.e., the spot weld furthest to the left) relative to the next spot weld adjacent to it (i.e., the next circle to the right) in a proximal direction may be greater relative to the distance separation between any adjacent spot welds of the remaining 5 weaker welds in a proximal direction. Increasing of the spacing of this last weld (furthest from the proximal end/tip of the inner tube) from the next adjacent weld reduces localized heating of the securement wire thereby reducing the heat affective zone (HAZ) of diminished integrity. It is therefore pointed out that the distance separation in an axial direction between any two adjacent spot welds (among adjacent stronger welds 560', among adjacent weaker welds 560, or between the weaker weld 560 and the adjacent stronger weld 560') may be varied, as desired. Once again referring to the example in FIG. 9, the 2 large welds (closest to the proximal end) provide a relatively large holding strength. However, these welds have an edge effect due to the HAZ, where the wire may break off at that point under load. The additional, smaller 5 welds (in a distal direction) distribute the load so that the HAZ border does not reduce the overall strength. Acting as a strain relief, in this example configuration the last two welds (furthest from the proximal end—furthest to the left) are spaced out/apart to aid in that distribution (creating a gradient of the load on the welds). This spacing need not always be employed but may be advantageous in certain applications. One factor in evaluating the number of welds (furthest from the proximal end) to be spaced apart from one another is the axial length of the weld window itself. That is, the longer the axial length of the weld window the more space available to be able to separate adjacent welds.

To sustain even greater forces, the strength of the one or more weld bond(s) (one or more supplemental connection points) between the securement wire and proximal inner tube may be enhanced by application of a biocompatible adhesive. Such modification calls for one or more secondary cutouts (e.g., laser cuts) (hereinafter referred to as "adhesive windows") to be made in the proximal inner tube. Preferably, each adhesive window is aligned in an axial direction with one another and separated radially approximately 180° from the weld window. The length in an axial direction of the adhesive window may vary so long as the adhesive is able to wick. For instance, the length in an axial direction of a single adhesive window or multiple adhesive windows together may span substantially the same length in an axial direction as that of the weld window. Alternatively, the length in an axial direction of a single adhesive window may be substantially smaller (e.g., a mere hole) relative to the larger length in an axial direction of the weld window. Preferably, each adhesive window substantially coincides/aligns/overlaps with the weld window.

Figure 8A:
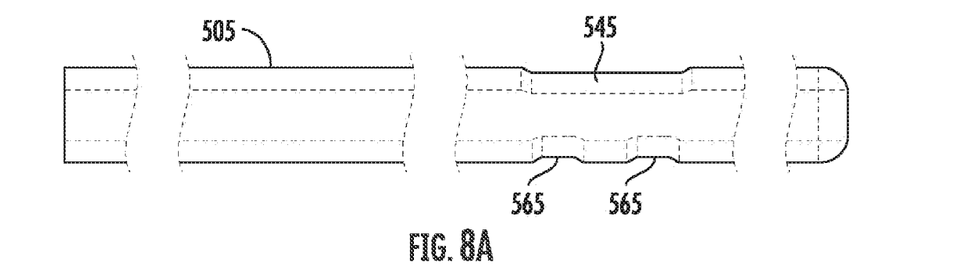
FIG. 8A is a side view of an exemplary proximal inner tube having two adhesive windows separated radially 180° from and axially aligned with that of a single weld window.
Figure 8B:
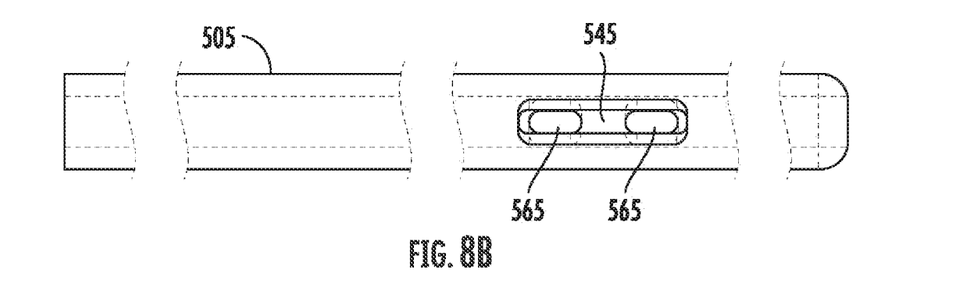
FIG. 8B is a top view of the proximal inner tube of FIG. 8A depicting the axial alignment of the two adhesive windows within the single weld window.

Referring to the side view of the example shown in FIG. 8A, two adhesive windows 565 are cutout radially inward of the proximal inner tube 505. As seen in the top view of FIG. 8B: (i) the length in a lateral direction of each adhesive window 565 is substantially equal to the length in a lateral direction of the weld window 545; (ii) in an axial direction each of the adhesive windows 565 coincides/aligns/overlaps within that of the weld window 545; and (iii) the adhesive windows 565 aligned with one another in an axial direction together as a unit are separated radially by approximately 180° from the weld window 545. With the one or more adhesive windows cutout the proximal tube is oriented on the chuck with the adhesive windows facing upwards. A biocompatible adhesive injected or deposited via the one or more adhesive windows 565 and wicks through the lumen of the proximal inner tube to the opposite side (e.g., 180 degrees in a radial direction) surrounding (flooding) the previously created one or more spot weld(s) forming a supplemental adhesive bond. As a result of the supplemental adhesive bond, even greater forces imparted on the securement wire during detachment may be sustained without disconnecting. As depicted in the exemplary configuration of FIGS. 8A & 8B, the proximal end of the weld window 545 is preferably approximately 1 mm from the proximal end of the proximal inner tube 505, while the distal end of the weld window 545 is approximately 1.6 mm from the proximal end of the proximal inner tube 505. Risk of breakage of the weakened wall of the proximal inner tube during use is mitigated with a weld window relatively small in length in an axial direction arranged relatively close to the proximal end of the proximal inner tube.

If the weld window is arranged closer to the outer delivery tube 510 (i.e., the proximal end of the weld window preferably being approximately 16 mm from the proximal end of the proximal inner tube) the construction of the proximal inner tube is weakened with increased potential for breakage. To reinforce or supplement the otherwise weakened wall of the proximal inner tube slack is intentionally added so that the proximal inner tube 505 may be telescopically pushed/slid in a distal direction within the lumen of the outer delivery tube 510 until the weld window 545 is concealed/hidden therein. Thereafter, the outer delivery tube 510 is crimped securing in position the proximal inner tube 505 therein. As a result, the weakened or fragile area of the wall of the proximal inner tube surrounding the weld and adhesive windows (along with the spot and adhesive welds created therein) are encased, concealed, protected, or shielded by the outer delivery tube providing both protection and rigidity/strength during regular use minimizing or eliminating any risk of breakage.

FIG. 10A is a side view (prior to loading of the implantable intravascular treatment device, e.g., embolic coil) with the securement wire 515 extending through the outer delivery tube 510 and secured by one or more laser welds (supplemental connection points generically represented as a single large circle exposed within the weld window) to the inner wall of the proximal inner tube 505. The proximal bead 570 may be welded to the proximal end of the proximal inner tube either independently of or at the time of creating the welds 560, 560'. At the time of creation of the one or more spot welds (supplemental connection points) allotted slack (e.g., approximately 0.3 mm) is preferably maintained in the securement wire (distally of the location of the welds) providing allowance for subsequent advancement as a unit of the proximal inner tube and securement wire secured thereto in a distal direction into the outer delivery tube. Preferably, the length in an axial direction from the proximal end/tip of the proximal inner tube to the distal edge of the weld window is preferably approximately 1.0 mm, while the proximal end of the proximal inner tube preferably extends in a proximal direction from the proximal end of the outer delivery tube by approximately 13 mm-approximately 16 mm.

Figure 10B:
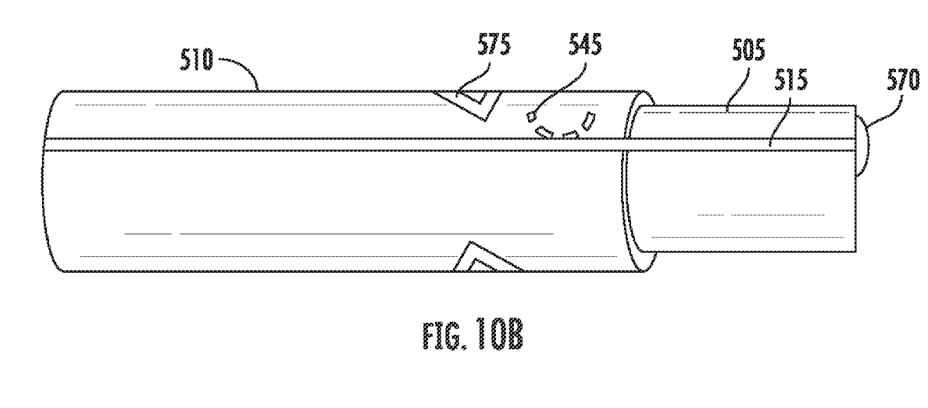
FIG. 10B is a side view representation, after loading of the implantable intravascular device, the proximal inner tube with the securement wire welded thereto telescopically advanced in a distal direction whereby the weld window (depicted by the dashed semicircle) is concealed/shielded/covered/protected by the outer delivery tube physically crimped to maintain the proximal inner tube in place in this concealing position.

Thereafter, the implantable intravascular treatment device (e.g., embolic coil) is loaded on to the delivery and detachment device. The proximal inner tube together with the securement wire secured thereto via the one or more spot welds (supplemental connection points) as a unit is then advanced in a distal direction until the entire weld window 545 (along with the adhesive windows, spot welds and adhesive welds) is fully concealed, protected, or shielded by the outer delivery tube 510 (hereinafter referred to as the "concealed position") (FIG. 10B). In the exemplary embodiment in FIG. 10B, the proximal inner tube 505 is advanced (axially slid or pushed in a distal direction) through the lumen of the outer delivery tube 510 by approximately 0.3 mm, whereby approximately 1.3 mm of the proximal inner tube 505 remains exposed (i.e., not concealed, protected, or shielded by the outer delivery tube). The proximal inner tube 505 and securement wire 515 together as a unit may be maintained in place in the concealed position by crimping 575 or otherwise radially mechanically compressing the outer delivery tube 510 reducing the inner diameter of its lumen distally of the distal edge of the weld window (represented in FIG. 10B by the dashed semi-circle).

The present inventive delivery and detachment system has been shown and described with respect to implantation of an embolic coil during a coil embolization procedure in the treatment of an intracranial aneurysm. It is contemplated and within the intended scope of the present invention to utilize the present inventive delivery and detachment system for delivering other types of implantable intravascular treatment devices used in other endovascular treatment procedures.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A delivery and detachment system for an implantable intravascular treatment device, the system comprising:
an outer delivery tube having a proximal end, an opposite distal end, and a lumen defined axially therein;
a proximal inner tube having a proximal end, an opposite distal end, and a lumen defined axially therein; the proximal inner tube being telescopically slidable within the lumen of the outer delivery tube; the proximal inner tube having a weld window radially inward cutout defined therein along an axial section thereof between but not including the proximal and distal ends; and
a securement wire disposed axially within the lumen of the proximal inner tube; a proximal end of the securement wire attached to the proximal end of the proximal inner tube via a proximal bead; and the securement wire secured to an inner wall of the lumen of the proximal inner tube via at least one supplemental connection point coinciding with the weld window.

2. The system in accordance with claim 1, wherein the at least one supplemental connection point is at least one spot weld.

3. The system in accordance with claim 2, wherein the at least one spot weld is a plurality of spot welds arranged in series in an axial direction and all positioned within the weld window.

4. The system in accordance with claim 3, wherein the plurality of spot welds are not all equal in size.

5. The system in accordance with claim 4, wherein of the plurality of spot welds at least one spot weld arranged closest to the proximal end of the proximal inner tube is larger in size relative to at least one spot weld arranged furthest from the proximal end of the proximal inner tube.

6. The system in accordance with claim 4, wherein the plurality of spot welds are arranged so that a separation distance between adjacent spot welds is not always equal.

7. The system in accordance with claim 6, wherein of the plurality of spot welds at least two adjacent spot welds arranged furthest from the proximal end of the proximal inner tube are separated from one another a distance greater than a distance separation of two adjacent spot welds arranged closer to the proximal end of the proximal inner tube.

8. The system in accordance with claim 1, wherein an axial length between the proximal end of the proximal inner tube and a proximal edge of the weld window is ≥approximately 1.0 mm.

9. The system in accordance with claim 1, wherein an axial length between the proximal end of the proximal inner tube and proximal edge of the weld window is in a range between approximately 13 mm and approximately 16 mm; and the proximal inner tube is telescopically arranged and secured in position within the outer delivery tube with the weld window and the at least one supplemental connection point fully concealed.

10. The system in accordance with claim 1, wherein the proximal inner tube has an adhesive window defined radially inward therein; the adhesive window being axially aligned and radially separated approximately 180 degrees from the weld window; and the at least one supplemental connection point being at least partially surrounded with adhesive.

11. A method of making a delivery and detachment system for an implantable intravascular treatment system including: an outer delivery tube having a proximal end, an opposite distal end, and a lumen defined axially therein; a proximal inner tube having a proximal end, an opposite distal end, and a lumen defined axially therein; the proximal inner tube being telescopically slidable within the lumen of the outer delivery tube; the proximal inner tube having a weld window radially inward cutout defined therein along an axial section thereof between but not including the proximal and distal ends; and a securement wire disposed axially within the lumen of the proximal inner tube; a proximal end of the securement wire attached to the proximal end of the proximal inner tube via a proximal bead; the securement wire being secured to an inner wall of the lumen of the proximal inner tube via at least one supplemental connection point coinciding with the weld window, the method comprising the steps of:

assembling the proximal inner tube telescopically in the lumen of the outer delivery tube so that the proximal end of the proximal inner tube extends beyond the proximal end of the outer delivery tube without concealing the weld window;

threading in a direction from the distal end to the proximal end of the proximal inner tube the securement wire and at least one positioning wire through the lumen of the proximal inner tube until the proximal end of each of the securement wire and the at least one positioning wire extends beyond the proximal end of the proximal inner tube;

forcing the securement wire in direct physical contact with an inner wall of the lumen of the proximal inner tube coinciding with the weld window by manipulating the securement wire and/or the at least one positioning wire;

within the weld window, creating at least one supplemental connection point between the securement wire and the inner wall of the lumen of the proximal inner tube along an axial section in direct physical contact with one another; and withdrawing in a proximal direction the at least one positioning wire from the proximal inner tube.

12. The method in accordance with claim 11, wherein the threading step comprises: (i) inserting the securement wire, prior to sequentially inserting one at a time each of the at least one positioning wire; (ii) inserting the securement wire, prior to inserting the at least one positioning wire altogether as a unit; or (iii) inserting the securement wire and the at least one positioning wire simultaneously altogether.

13. The method in accordance with claim 11, wherein the at least one supplemental connection point is at least one spot weld.

14. The method in accordance with claim 13, wherein the at least one spot weld is a plurality of spot welds arranged in series in an axial direction and all positioned within the weld window.

15. The method in accordance with claim 14, wherein the plurality of spot welds are not all equal in size.

16. The method in accordance with claim 15, wherein of the plurality of spot welds at least one spot weld arranged closest to the proximal end of the proximal inner tube is larger in size relative to at least one spot weld arranged furthest from the proximal end of the proximal inner tube.

17. The method in accordance with claim 14, wherein the plurality of spot welds are arranged so that a separation distance between adjacent spot welds is not always equal.

18. The method in accordance with claim 17, wherein of the plurality of spot welds at least two adjacent spot welds arranged furthest from the proximal end of the proximal inner tube are separated from one another a distance greater than a distance separation of two adjacent spot welds arranged closer to the proximal end of the proximal inner tube.

19. The method in accordance with claim 11, wherein an axial length between the proximal end of the proximal inner tube and a proximal edge of the weld window is ≥approximately 1.0 mm.

20. The method in accordance with claim 11, wherein an axial length between the proximal end of the proximal inner tube and proximal edge of the weld window is in a range between approximately 13 mm and approximately 16 mm; and the method further comprises the step of telescopically sliding in a distal direction the proximal inner tube in the lumen of the outer delivery tube so that the weld window is fully concealed within the outer delivery tube; and securing in position the proximal inner tube in the outer delivery tube.

21. The method in accordance with claim 11, further comprising the steps of:

introducing an adhesive via an adhesive window defined radially inward in the proximal inner tube; the adhesive window being aligned in an axial direction with and radially separated approximately 180 degrees from the weld window; and wicking of the introduced adhesive through the lumen of the proximal inner tube surrounding the at least one supplemental connection point.

* * * * *